(12) United States Patent
Davidson et al.

(10) Patent No.: US 7,756,657 B2
(45) Date of Patent: Jul. 13, 2010

(54) SYSTEM FOR STORING AND PRESENTING SENSOR AND SPECTRUM DATA FOR BATCH PROCESSES

(75) Inventors: Mikael H. Davidson, Lakewood, OH (US); Hemant Kanodia, Solon, OH (US); Thomas Buijs, Quebec (CA); Claude LaFond, Quebec (CA)

(73) Assignee: ABB Inc., Cary, NC (US)

( * ) Notice: Subject to any disclaimer, the term of this patent is extended or adjusted under 35 U.S.C. 154(b) by 228 days.

(21) Appl. No.: 11/939,696

(22) Filed: Nov. 14, 2007

(65) Prior Publication Data

US 2008/0161958 A1 Jul. 3, 2008

Related U.S. Application Data

(60) Provisional application No. 60/858,974, filed on Nov. 14, 2006.

(51) Int. Cl.
*G06F 19/00* (2006.01)
*G01N 37/00* (2006.01)
*G05B 21/02* (2006.01)

(52) U.S. Cl. .......................................... 702/83; 700/73

(58) Field of Classification Search .................. 700/73, 700/108; 702/27, 83
See application file for complete search history.

(56) References Cited

U.S. PATENT DOCUMENTS

| | | | |
|---|---|---|---|
| 5,058,043 A | 10/1991 | Skeirik | |
| 6,037,592 A * | 3/2000 | Sunshine et al. | 250/343 |
| 6,148,239 A | 11/2000 | Funk et al. | |
| 6,363,294 B1 * | 3/2002 | Coronel et al. | 700/121 |
| 6,587,744 B1 | 7/2003 | Stoddard et al. | |
| 6,608,670 B2 * | 8/2003 | Nottke et al. | 356/71 |
| 6,630,672 B1 | 10/2003 | Brotherton et al. | |
| 6,643,391 B2 * | 11/2003 | Anderson et al. | 382/129 |
| 6,647,315 B1 * | 11/2003 | Sherriff et al. | 700/204 |
| 6,834,370 B1 * | 12/2004 | Brandl et al. | 715/201 |
| 6,862,562 B1 * | 3/2005 | Treiber et al. | 703/12 |
| 6,978,210 B1 * | 12/2005 | Suter et al. | 702/13 |
| 7,085,615 B2 * | 8/2006 | Persson et al. | 700/108 |
| 7,117,100 B2 * | 10/2006 | Venkataraman et al. | 702/27 |
| 7,194,369 B2 * | 3/2007 | Lundstedt et al. | 702/104 |
| 7,221,988 B2 * | 5/2007 | Eryurek et al. | 700/108 |
| 7,249,356 B1 | 7/2007 | Wilson et al. | |
| 7,275,420 B2 * | 10/2007 | Discenzo | 73/54.28 |
| 7,315,369 B2 * | 1/2008 | Battiste | 356/301 |
| 7,346,404 B2 * | 3/2008 | Eryurek et al. | 700/65 |
| 7,359,759 B2 * | 4/2008 | Cheng et al. | 700/121 |
| 7,395,131 B2 * | 7/2008 | Funk | 700/108 |

(Continued)

*Primary Examiner*—Crystal J Barnes-Bullock
(74) *Attorney, Agent, or Firm*—Paul R. Katterle

(57) ABSTRACT

A system for monitoring and controlling a batch process. The system includes a control system that is operable to control the batch process and to receive measured process variables of the batch process. An analyzer analyzes a material sample from the batch process and generates array data representative of the composition of the material sample. An analyzer controller is operable to collect the array data from the analyzer and the measured process variables from the control system. A software data server running on a computer is operable to retrieve the array data and the measured process variables from the analyzer controller. A software information management system running on the computer is operable to receive the measured process variables and the array data from the data server and to store the measured process variables and the array data in a database in an associated manner.

13 Claims, 12 Drawing Sheets

U.S. PATENT DOCUMENTS

| | | |
|---|---|---|
| 7,680,970 B2 * | 3/2010 | Sherriff et al. .............. 710/240 |
| 2002/0077711 A1 | 6/2002 | Nixon et al. |
| 2003/0068825 A1 * | 4/2003 | Washburn et al. ............. 436/86 |
| 2004/0267395 A1 * | 12/2004 | Discenzo et al. ............. 700/99 |
| 2007/0162232 A1 * | 7/2007 | Patterson et al. ............... 702/1 |
| 2007/0283030 A1 * | 12/2007 | Deininger et al. ........... 709/230 |
| 2008/0066019 A1 * | 3/2008 | Worek et al. ................ 715/965 |
| 2008/0127186 A1 | 5/2008 | Kanodia et al. |

* cited by examiner

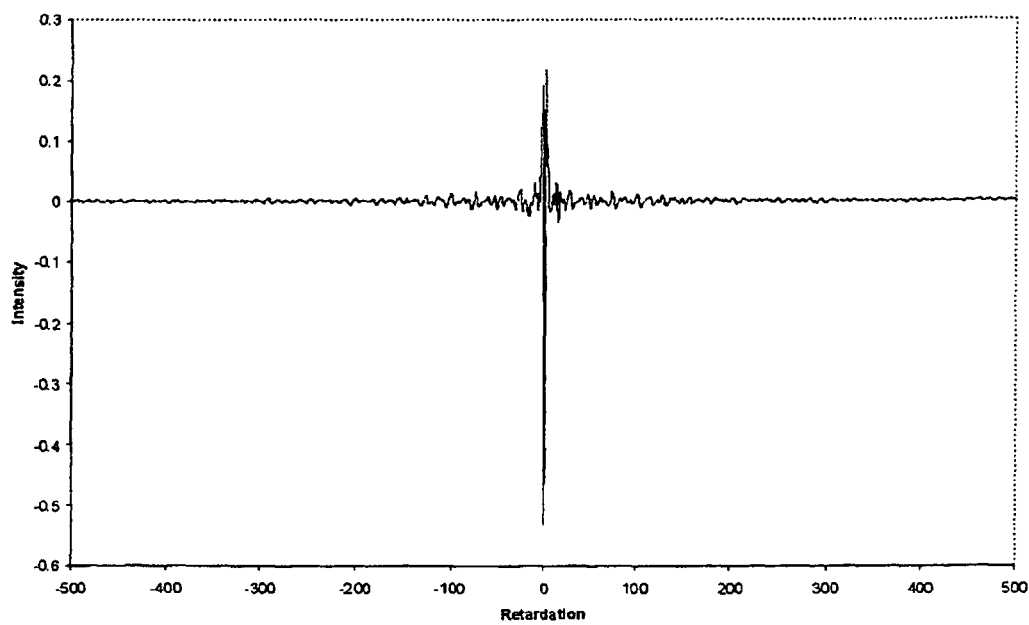
Fig. 1  An Interferogram.
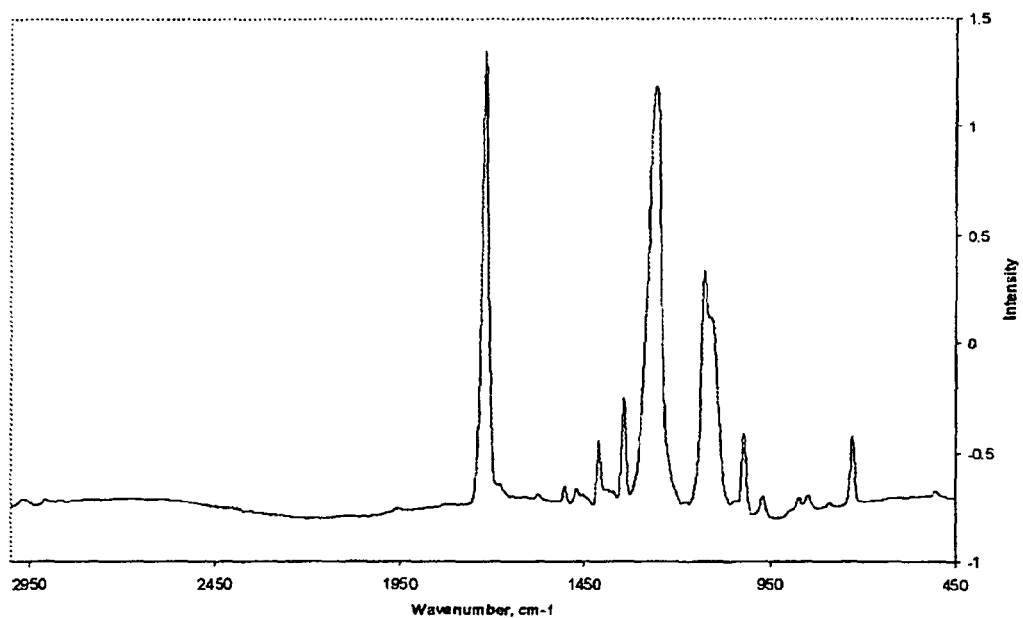
Fig. 2  A typical IR Spectrum

SYSTEM FOR STORING AND PRESENTING SENSOR AND SPECTRUM DATA FOR BATCH PROCESSES

CROSS-REFERENCE TO RELATED APPLICATION

This application claims the benefit of U.S. provisional patent application No. 60/858,974 filed on Nov. 14, 2006, which is hereby incorporated by reference in its entirety.

BACKGROUND OF THE INVENTION

The present invention is directed toward batch processes and, more particularly, toward a system for storing and presenting sensor and spectral data for batch processes.

A batch process is a process in which a limited quantity of ingredients are added and processed in a step-wise fashion. A recipe defines the equipment, procedures and formula used to run a batch process. An automated batch process is typically controlled by a process control system having controller subsystems for controlling the valves, pumps and other physical equipment required to perform the batch process. When a plurality of batch processes are being run to produce a plurality of different products, a software batch management application is typically provided to interface with the process control system. In such a case, the controller subsystems store and execute control logic for executing procedures within the batch process (such as delivering ingredients to a reactor), while the batch management application will allocate and de-allocate equipment, store recipes, schedule batch processes, generate reports, and store and archive batch data. The batch management application may also provide process variable setpoints to controller subsystems and may control the execution of batch procedures, such as stopping a current batch procedure, or starting a subsequent batch procedure.

During or after the run of a batch process, it is often desirable to analyze the product of the batch process to ascertain its composition. The composition of the product may be used to control the batch process, to improve the batch process and/or to comply with governmental regulations. The product of a batch process is typically analyzed using a spectrometer. A spectrometer is a device that is used to determine the chemical composition of a sample using electromagnetic radiation, e.g., light. In a spectrometer, electromagnetic radiation is interacted with a sample to produce a spectrum that is detected and then analyzed to determine the composition of the sample. An emission spectrometer excites molecules of a sample to higher energy states and then analyzes the radiation emitted when the molecules decay to their original energy state. An absorption spectrometer passes light through a sample and measures the absorption of light at various wavelengths. In a dispersive type of absorption spectrometer, the light is separated into its component wavelengths using a prism or a holographic grating and the absorption at each wavelength is individually measured. In an interference type of absorption spectrometer, modulated light having a range of different wavelengths is passed through a sample to obtain a combined measurement of the absorption at the different wavelengths. The combined measurement is then converted into a spectrum using Fourier transform computations. This interference type of absorption spectrometer typically utilizes infrared light and, thus, is known as a Fourier transform infrared (FTIR) spectrometer.

An FTIR spectrometer typically includes a Michelson interferometer or other similar type of interferometer that splits a broadband beam of infrared light into two parts. A Michelson interferometer has four arms. A first arm contains a source of infrared light (such as a quartz-halogen bulb), a second arm contains a stationary (fixed) mirror, a third arm contains a moving mirror and a fourth arm is open. At the intersection of the four arms is a beam splitter that is constructed to transmit half of the impinging radiation and reflect the other half of the impinging radiation. The transmitted light beam strikes the fixed mirror and the reflected light beam strikes the moving mirror. After reflecting off the respective mirrors, the two light beams recombine at the beam splitter. The combined light beam is then directed through a sample cell containing the sample to be analyzed, which modifies the interference pattern of the combined beam. The modified beam then impinges on a detector.

For each wavelength of light, the distance traveled by the light from the moving mirror changes so as to be in and out of phase with the light from the fixed mirror, which causes the intensity of the wavelength of the combined light beam to change in a sinusoidal manner due to the additive nature of waves. For each wavelength, a plot of light intensity versus optical path difference for one scan of the moving mirror is called an interferogram. A scan of the moving mirror is one complete movement of the mirror along its travel path.

Since the light used in the interferometer has a plurality of different wavelengths, the detector measures a total interferogram, which is the summation of all the interferograms from all the different infrared wavelengths. Thus, the total interferogram is a sum of sinusoidal waves, each of which contains information about the wavenumber of a given infrared peak and amplitude information about the peak intensity at that wavenumber. The Fourier transform computations transform the summed sinusoidal waves into a raw spectrum. This raw spectrum not only contains information about the sample, but about the spectrometer as well. To obtain information only about the sample, another calculation is performed using a reference or background spectrum. A background spectrum is taken before starting the analysis of the sample, when there is no sample in the cell (or there is a blank sample). The background spectrum only contains information about the spectrometer, including the sample cell, etc. The raw spectrum is ratioed against the background spectrum to produce a transmittance spectrum, which is then converted to an absorbance spectrum in the form of absorbance versus wavenumber. FIG. 1 shows an interferogram for a sample and FIG. 2 shows the absorbance spectrum of the sample. The interferogram, the raw spectrum and the absorbance spectrum from an FTIR spectrometer may be collectively referred to as "spectral data".

The absorbance spectrum is used to determine the presence and concentration of a chemical species, or analyte, within a sample based on the wavenumber or range of wavenumbers absorbed and the magnitude of the absorbance of particular spectral regions. In other words, an analyte will absorb radiation in particular spectral regions creating a characteristic spectral profile according to the chemical structure of the analyte. A chemometric model determined for an analyte calculates the concentration of that analyte as a function of the magnitude of the absorbance in these spectral regions. The chemometric model is determined using multivariate mathematical correlation techniques to develop the model based on spectral measurements of a number of standards wherein the concentration of the analyte being modeled is known Typically, the spectral data from a spectrometer in a batch process is only stored if required for regulatory audit purposes. If stored, the spectral data is conventionally stored separate from other information about the batch process, such as sensor data (temperature, pH, pressure, etc.) and batch management data (e.g., batch start, batch stop, batch abort, batch runtime, equipment used, etc.).

It would therefore be desirable, to provide a system for use with a batch process, wherein the system stores spectral data from a spectrometer in association with sensor data and batch management data. The present invention is directed to such a system.

SUMMARY OF THE INVENTION

In accordance with the present invention, a system for monitoring and controlling a batch process is provided. Field instruments and a sample system are connected to the batch process. The field instruments are operable to measure process variables of the batch process and the sample system is operable to obtain a sample of material being produced by the batch process. The system includes a control system for controlling the batch process. The control system is connectable to the field instruments to receive the measured process variables therefrom. An analyzer is connectable to the sample system to receive the material sample therefrom. The analyzer is operable to analyze the material sample and to generate array data representative of the composition of the material sample. An analyzer controller is connectable to the analyzer and to the control system and is operable to collect the array data from the analyzer and the measured process variables from the control system. At least one computer is connectable to the analyzer controller and to the control system. A software data server is stored on the at least one computer and is executable to retrieve the array data and the measured process variables from the analyzer controller. A software information management system is stored on the at least one computer and includes a database. The information management system is executable to receive the measured process variables and the array data from the data server and to store the measured process variables and the array data in the database in an associated manner.

BRIEF DESCRIPTION OF THE DRAWINGS

The features, aspects, and advantages of the present invention will become better understood with regard to the following description, appended claims, and accompanying drawings where:

FIG. 1 shows an interferogram for a sample;

FIG. 2 shows the absorbance spectrum of the sample;

DETAILED DESCRIPTION OF ILLUSTRATIVE EMBODIMENTS

Figure 3:
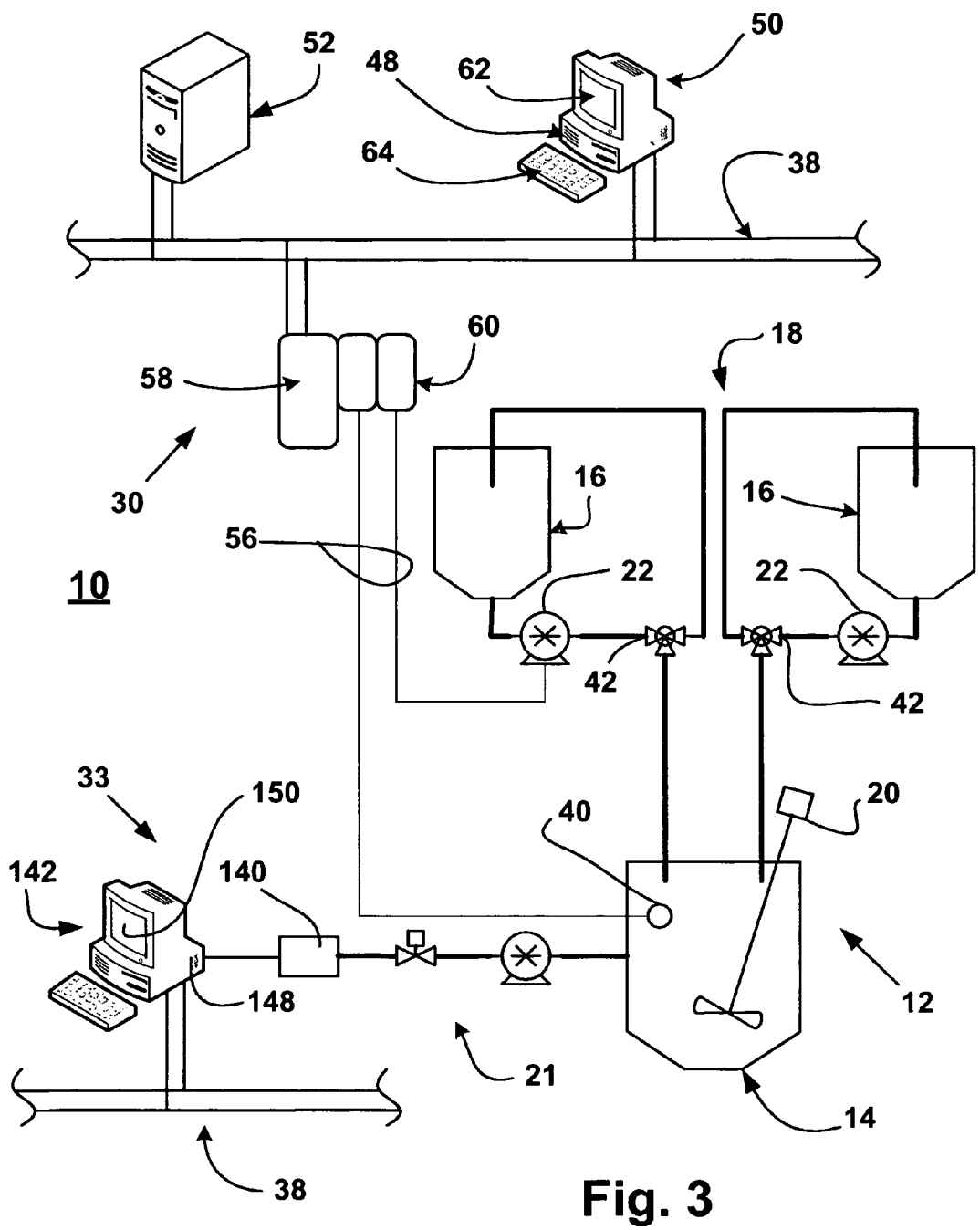
FIG. 3 is a schematic view of a batch process connected to a system for monitoring and controlling the batch process.

It should be noted that in the detailed description that follows, identical components have the same reference numerals, regardless of whether they are shown in different embodiments of the present invention. It should also be noted that in order to clearly and concisely disclose the present invention, the drawings may not necessarily be to scale and certain features of the invention may be shown in somewhat schematic form.

As used herein, the following terms shall have the following meanings:

"batch process" shall mean a process in which a limited quantity of ingredients are added and processed in a step-wise fashion;

"batch run" shall mean a performance of a batch process;

"recipe" shall mean an identification of the equipment, procedures and formula used to run a batch process;

"header" shall mean a component of a recipe identifying the product produced by the batch process;

"batch" shall mean, as appropriate for the context, a batch run, or the product produced thereby;

"batch campaign" is a series of batch runs using the same recipe.

Referring now to FIG. 3 there is shown schematic drawing of a portion of an enterprise 10 that can benefit from the use of the present invention. The enterprise includes a process cell 12 operable to perform one or more batch processes. The process cell 12 includes a mixing vessel or reactor 14, a plurality of ingredient storage tanks 16, and a piping system 18 connecting the ingredient storage tanks 16 to the reactor 14. The reactor 14 includes a stirring device 20 for mixing ingredients during the batch process. The piping system 18 has pumps 22 for pumping ingredients from the ingredient storage tanks 16 to the reactor 14. The batch processes may be processes for the manufacture of beer, paint, pharmaceutical compounds, specialty chemicals, or other types of batch-made products.

Figure 4:
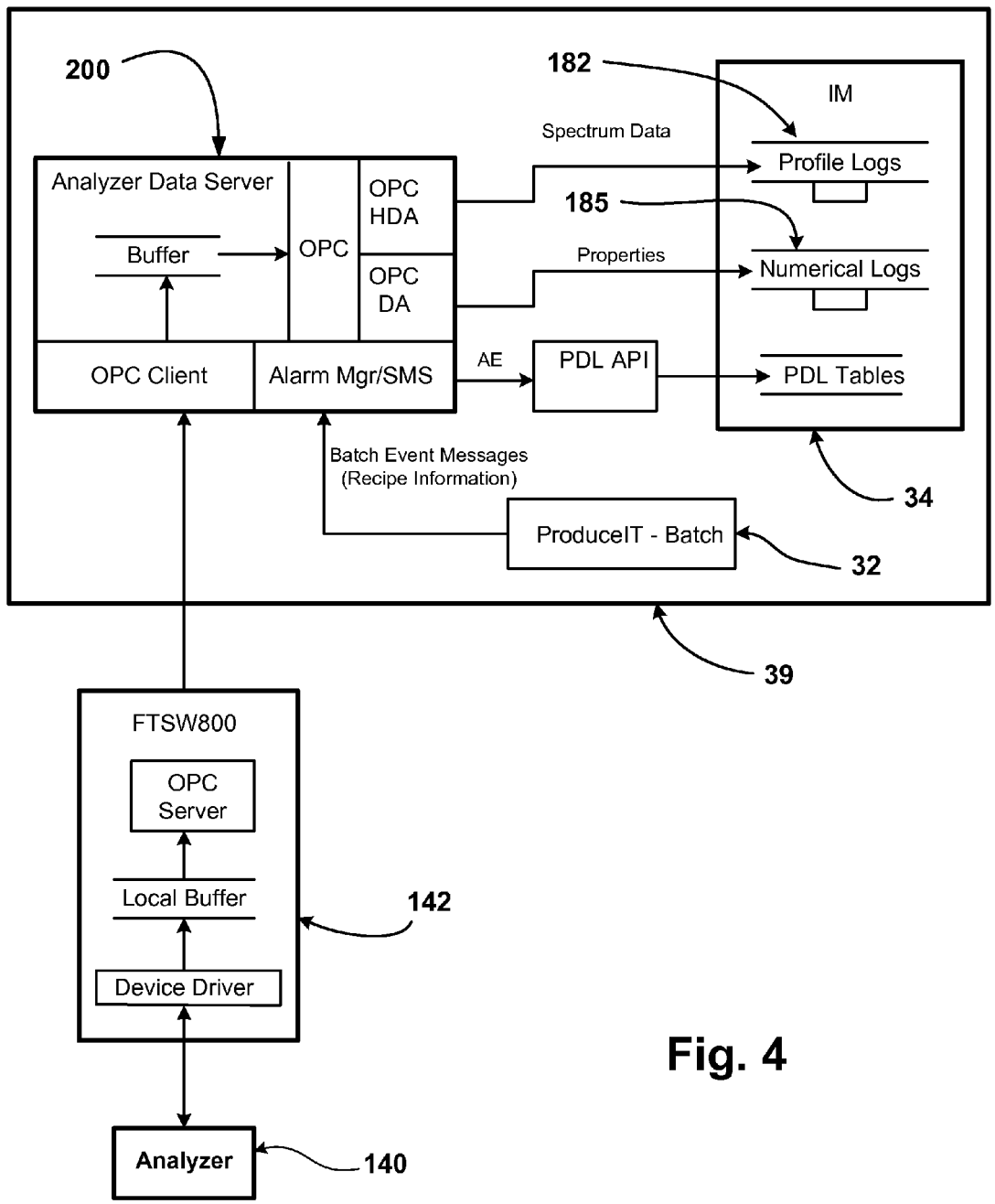
FIG. 4 is a schematic view of an analyzer connected by an analyzer controller to an automation software system embodied in accordance with the present invention.

Reference is now also made to FIG. 4. For purposes of monitoring and controlling the process cell 12, the enterprise 10 is provided with process field devices, a sample system 21, an analysis system 33, a distributed control system (DCS) 30 and an automation software system 39 that includes a batch system 32 and an information management system 34. The automation software system 39 is stored in and runs on one or more computers having at least one interface device, such as a keyboard, and a display screen for displaying information to a user. In the embodiment shown in FIG. 3, some components of the automation software system 39 are stored in and run on a server computer 52 and other components are stored in and run on a client workstation 50.

Process Field Devices.

The process field devices include monitoring devices (such as sensors 40) and control devices (such as valves 42) for monitoring and controlling the batch processes. The process field devices communicate operating values of the batch process to the DCS 30 over a field network 56, which may utilize shielded twisted pair wires, coaxial cables, fiber optic cables, or wireless communication channels.

Sample and Analysis Systems

The sample system 21 is connected to the reactor 14 to obtain samples of the batch product being produced therein. The sample system 21 may include valves, piping and pumps, as well as sensors for measuring properties of the samples, such as temperature, pH, etc. The sample system 21 is connected to the analysis system 33 to provide the samples to the analysis system 33.

Figure 5:
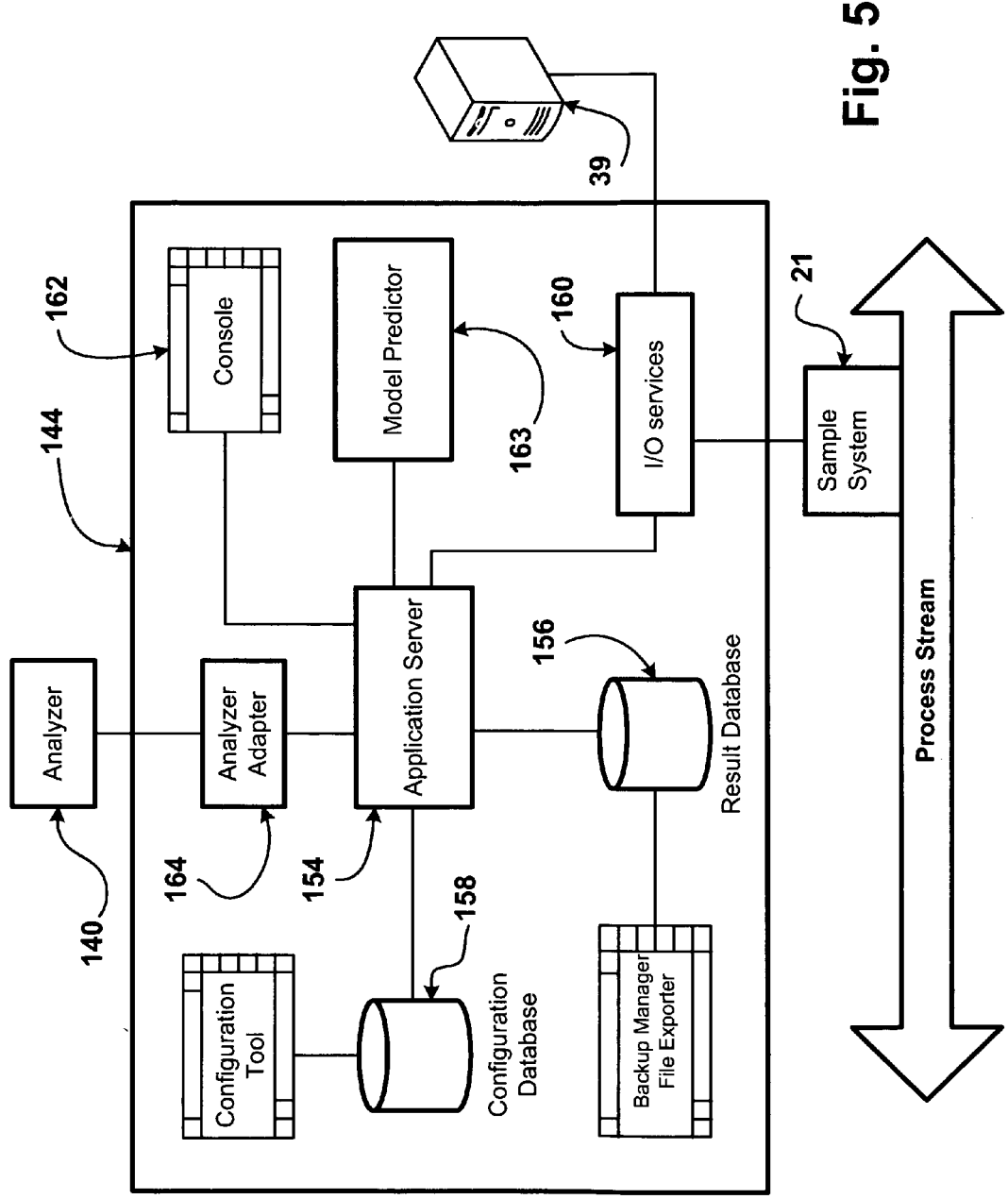
FIG. 5 is a schematic view of a controller software system of the analyzer controller.
Figure 6:
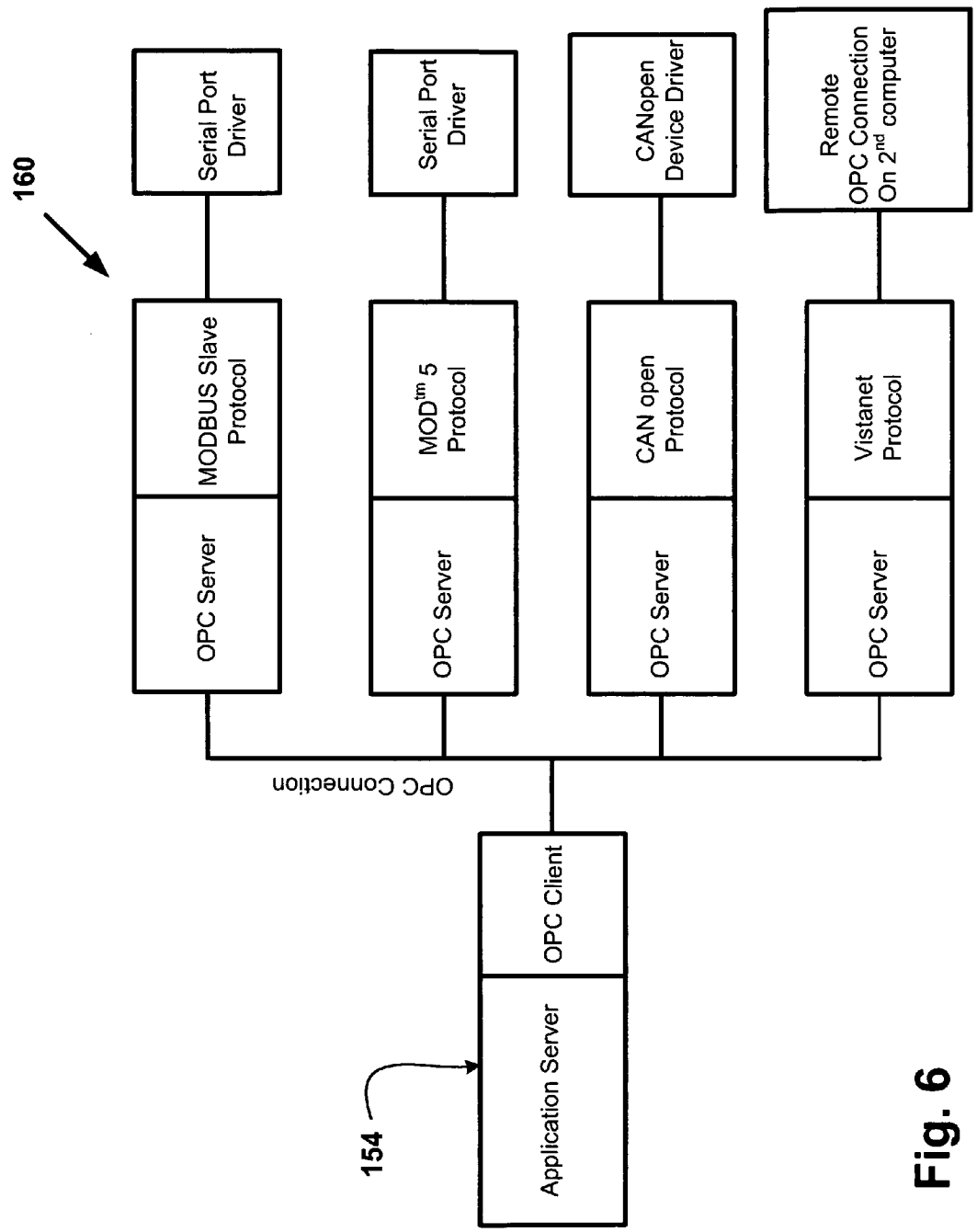
FIG. 6 is a schematic view of I/O services of the controller software system.

The analysis system 33 includes one or more spectrometers 140 and one or more analyzer controllers 142. The spectrometers 140 may be FTIR spectrometers that are operable to generate absorption spectrums for the samples. The analyzer controllers 142 run applications that obtain absorption spectrums and other information from the spectrometers 140 and makes this data available to the automation software system 39. An application running on an analyzer controller 142, inter alia, specifies a particular spectrometer 140, the data to be collected from the spectrometer 140 (e.g., absorption spectrum), the data collection interval (e.g., every ten minutes) and the data collection period (e.g., one week). An application may also specify sensor data associated with the spectrometer 140 that is to be collected. The sensor data is obtained from the DCS 30 over the network 38. The analyzer controller 142 comprises a computer having a controller software system 144 (shown in FIG. 5) running thereon. The analyzer controller 142 includes a processor 148 and a monitor 150. Referring now to FIG. 5, the controller software system 144 includes an application server 154, a result database 156, a configuration database 158, I/O services 160, a console GUI 162, a model predictor 163 and analyzer adapters 164 that include drivers for the spectrometers 140. The application server 154 performs all of the logic, scheduling and computations for the applications. The model predictor 163 applies chemometric models to absorption spectra to obtain the chemical compositions of samples. The results of the applications are stored in the result database 156, which is implemented as a Microsoft SQL server database and a series of files. Referring now to FIG. 6, the I/O services 160 includes one or more OPC DA servers to read and write I/O values. The I/O services 160 permit the application server 154 to communicate with the automation software system 39 and other devices and computer programs. All of the I/O services are based on the OPC protocol.

Distributed Control System.

The DCS 30 interacts with the batch system 32, the analysis system 33 and the information management system 34, and is operable to: store and execute control logic for procedures of a recipe for a batch process; send transaction messages to the batch system at the end of a phase; react to abnormal conditions; and generate exception and event messages and alarms. The DCS 30 generally includes one or more controllers 58 and associated control devices, as well as a graphical operator control interface (operator workplace 84) that forms part of the automation software system 39. Input signals from the field devices are communicated over the field network 56 to the network 38 by 4-20 mA signaling and/or by one or more of the conventional control protocols, such as the HART® protocol, the Foundation™ Fieldbus protocol, or the Profibus protocol. For any of the field devices communicating via the Foundation™ Fieldbus protocol, the field network 56 comprises HSE/H1 linking devices, which connect the field devices to a high speed Ethernet subnet, which is connected to the network 38 through an FF HSE communication interface of the controller(s) 58 or through an FF OPC server (not shown). For any field devices communicating via the Profibus protocol, the field network 56 comprises DP/PA linking devices, which connect the field devices to a Profibus-DP line, which is connected to the network 38 through a Profibus communication interface of the controller(s) 58 or through a Profibus OPC server (not shown). For any field devices communicating via 4-20 mA signaling and/or the HART® protocol, the field network 56 typically comprises shielded twisted pair wires, which connect the field devices to an I/O subsystem 60, which includes one or more I/O modules with one or more associated module termination units, as is shown in FIG. 3. The I/O subsystem 60 is connected by a module bus to the controller(s) 58, which is/are connected to the network 38.

The network 38 interconnects the client work station 50, the server computer 52, the analyzer controllers 142, and the controller(s) 58. The network 38 includes a pair of redundant Ethernet cables over which information is communicated using the Manufacturing Message Specification (MMS) communication protocol and a reduced OSI stack with the TCP/IP protocol in the transport/network layer. Together, the network 38 and the field network 56 help form a communication link over which information may be transmitted between the field devices and clients.

The controller(s) 58 contain control programs for controlling the batch processes of the enterprise 10. The control programs utilize operating values from the field devices, which are received by the controller(s) 58 from the I/O subsystem 60. The control programs are written in one or more of the five IEC 61131-3 standard languages: Ladder Diagram, Structured Text, Function Block Diagram, Instruction List and Sequential Function Chart. Outputs from the control programs are transmitted to the control devices of the process field devices over the field network 56.

The client work station 50 is a personal computer (PC) with a central processing unit (CPU) 48, a monitor 62 for providing visual displays to an operator and a keyboard 64 for manually entering data. The CPU 48 has an operating system running thereon, which may be a Windows® operating system available from Microsoft Corporation.

In addition to the batch system 32 and the information management system 34, the automation software system 39 includes a graphical user interface (GUI) 66, a connectivity server 72, an aspect server 74, an analytical data server 200, a data export tool 220 and a data visualization tool 222. The batch system 32, the information management system 34, the connectivity server 72, the aspect server 74 and the analytical data server 200 run on the server computer 52, while the GUI 66, the data export tool 220 and the data visualization tool 222 run on the client work station 50.

Figure 7:
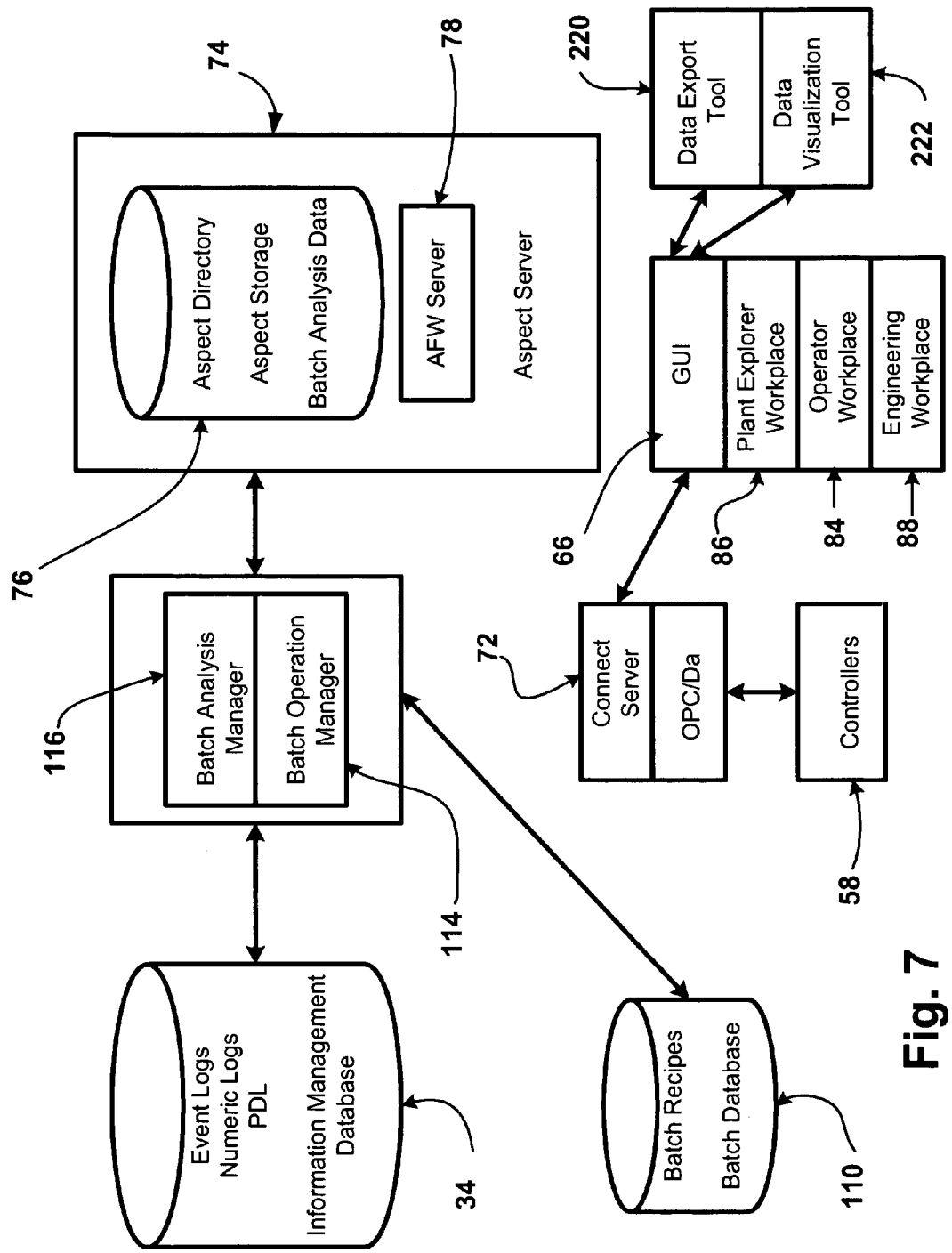
FIG. 7 is a schematic view of the automation software system.

Referring now also to FIG. 7, the connectivity server 72 includes an OPC server network based on Microsoft's OLE (now Active X), COM, and DCOM technologies. The OPC server network includes a controller OPC server that makes information from the controller(s) 58 available to any OPC client connected to the network 38, such as the analyzer controllers 142. As set forth above, an FF OPC server and/or a Profibus server may also be provided to connect the field devices to the network 38 without having to be connected to the controller(s) 58. The FF OPC server and the Profibus server are also based on Microsoft's OLE (now Active X), COM, and DCOM technologies that make information available to any OPC client on the network 38.

The analytical data server 200 is an OPC server and provides the spectral data, sensor data, and calculated composition data from the analyzer controllers 142 to OPC clients, such as the information management system 34, using OPC.

The analytical data server 200 communicates with the analyzer controllers 142 using a TCP/IP protocol. The configuration file is edited with a text editor to specify the computer names or IP addresses of the analyzer controllers 142. On startup, the executable reads the configuration file and begins sending a request message to each specified analyzer controller 142. In response, each analyzer controller 142 sends a reply message. The first request is for the 'status' of the analyzer controller 142. The 'status' reply includes the start time of the analyzer controller 142, which the analyzer data server 200 encrypts to generate an authentication key used in subsequent requests sent to that analyzer controller 142. The analyzer data server 200 then requests a configuration from the analyzer controller 142. The configuration contains a list of I/O items read and written by the analyzer controller 142, plus an optional list of usernames and encrypted passwords with user read and write permissions for I/O items.

If the application server 154 of an analyzer controller 142 is restarted with a new configuration, the analyzer data server 200 will have a request rejected due to invalid authentication (new start time). As a result, the analyzer data server 200 will re-request the status and then re-request the configuration. This ensures automatic updating of configurations in the analyzer data server 200.

Periodically, the analyzer data server 200 requests a refresh of time-stamped I/O item values which are more recent than a specified time. A reply from an analyzer controller 142 returns its current time (used in the next refresh request) and the list of time-stamped I/O item values. The first request specifies time zero to get all I/O item values and subsequent requests use the time returned in the last reply.

In addition to the periodic updates, an OPC client may explicitly read a list of OPC items to an analyzer controller 142 or write values to a list of OPC items of the analyzer controller 142. The analyzer data server 200 verifies the OPC client's read and write permissions for each OPC item. If the OPC client is permitted to read or write the OPC items, the read or write request is forwarded to the analyzer controller 142.

For increased reliability, the analyzer data server 200 can use redundant network connections to each analyzer controller 142. When both primary and backup connections are working, the analyzer data server 200 alternates use of the primary and backup connections. When neither primary nor backup connection is working, the analyzer data server 200 repeatedly alternates between checking the primary and backup connections until one connection works. When only one of two connections is working, the analyzer data server 200 uses that connection while periodically testing the failed connection until the failed connection works.

The analyzer data server 200 implementation separates the OPC DA interfaces from the analyzer controller 142 Application Programming Interface (API), allowing the OPC DA clients to be unaffected by any changes in the API. The analyzer data server 200 creates an OPC server object for each connected OPC client. The OPC client can browse the available OPC items which represent the I/O items in the connected analyzer controller 142. Each analyzer controller 142 must have a unique name which is used as the branch of a tree and the prefix to all OPC items belonging to that analyzer controller 142. This allows multiple analyzer controllers 142 to have identical I/O names which are seen as different OPC items in the analyzer data server 200.

The analyzer data server 200 has a single system object with zero or more device objects, zero or more tag objects, a tag 'tree', and a tag index. The tag 'tree' is browsed by OPC DA clients. The tag index is an alphanumeric sorted list of tag names, allowing each tag to quickly be found by its unique name. Each tag object represents one I/O point in a spectrometer 140. This code is generic to different OPC DA servers.

The analyzer data server 200 implements FtirDevice objects to communicate with the analyzer controllers 142 and FtirTag objects to represent the analyzer controller 142 I/O items. For spectral data, the FtirTag maintains a list of many simpler tag objects representing the different components of the complex spectral data. Since each tag is a potential OPC item in an OPC group, the list of available tags (OPC items) is greater than the list of I/O items in an analyzer controller 142.

An additional feature of the analyzer data server 200 is to automatically update a tag's quality (OPC item quality) to reflect the status of the connection to the tag's analyzer controller 142.

The aspect server 74 includes an aspect directory 76 containing all aspect objects and their aspects, as well as an aspect framework (AFW) server 78. The AFW server 78 is operable to wrap together HTML pages (aspects) for an object in a web-compliant AFW file that can be launched from an object tree 80 in the GUI 66. The aspect server 74 implements a method of organizing information using aspect objects (or simply "objects") and aspects associated with the objects. An object represents physical matter (such as a valve 42) or virtual matter (such as a function) and acts as a holder or container for information (such as run time data) concerning the object. Information concerning an object is contained in its aspects. An aspect is an assembly of information describing certain properties of an object, such as functional properties, physical construction properties and location properties. Information in an aspect is presented in a view, which may be a list, a table, a diagram, a drawing, or a graphic. An aspect may have more than one view.

In the GUI 66, objects and aspects are graphically represented by icons. In the description below, when reference is made to an object or aspect, it should be understood that the reference may be to the icon for the object or aspect and/or to its associated object or aspect, depending on the context.

The GUI 66 has a client/server architecture and has communication based on OPC. A suitable graphical user interface that may be utilized for the GUI 66 is Process Portal™, which is commercially available from the assignee of the present invention, ABB Inc. The GUI 66 has a plurality of workplaces that may be utilized. Each workplace comprises a collection of user-interactive functions (such as tool bars, faceplates, windows, pull-down menus, buttons, scroll bars, iconic images, wizards, etc.) that are combined for a particular use, such as controlling a batch process, maintaining an asset (such as a pump 22) in the enterprise 10, or configuring a model of the enterprise 10. Enterprise personnel may select a particular workplace from a workplace login page of the GUI 66. Three of the workplaces that may be selected are an operator workplace 84, a plant explorer workplace 86 and an engineering workplace 88. The plant explorer workplace 86 is used to explore and build hierarchically structured models of the enterprise 10, while the operator workplace 84 is configured for process operators responsible for controlling the batch processes. The engineering workplace 88 includes tools for implementing and servicing control configurations. The plant explorer workplace 86 and the engineering workplace 88 each include a main window 90 comprising an application bar 92 and a plurality of frames or areas, including an object area 94, an aspect list area 96 and, selectably, a preview area 100. The application bar 92 includes a fixed display area, a tool collection and shortcuts. The object area 94 is where an object browser displays the object tree 80, which is a list or tree of objects for a selected object structure (functional, locational or control), with each root object at a top level and its child objects at a lower or leaf level. An object can be accessed by right clicking on the object in an object tree 80, which opens a context menu containing a number of actions that can be performed. The aspect list area 96 displays all aspects of a currently selected object in an object tree 80. If the preview area 100 is enabled, the preview area 100 displays the view of an aspect currently selected in the aspect list area 96. If the preview area 100 is not enabled, the view of a selected aspect is displayed as a pop-up window. The view of an aspect can also be displayed in the main window 90.

Batch System

The batch system 32 is a software system that configures, runs and manages batch processes performed by the process cell 12. The batch system 32 configures batch processes by planning, organizing and designing batch control schemes for use by the DCS 30 in controlling the batch processes. The batch system 32 runs and manages batch processes by: scheduling batches; ensuring that equipment needed by one batch process is not being used by another batch process; guiding the DCS 30 through the steps or phases of a batch recipe; transmitting values for the various parameters in the batch recipes to the DCS 30; generating batch reports; and archiving batch data. The batch system 32 comprises a batch database 110 that stores batch recipes a batch operation manager 114, a batch analysis manager 116 and a batch client that is integrated into the GUI 66. The batch operation manager 114 has four functional areas: batch operation, recipe management, equipment configuration and batch production history.

The batch system 32 produces recipes for batch processes using an object oriented approach. More specifically, a recipe is produced using a graphical programming routine, wherein a recipe procedure diagram (RPD) 120 is drawn using graphical blocks, each of which is a software routine. The graphical blocks represent operations (sub-recipes), phases and batch manager actions. Batch manager actions (BMA) include allocating hardware resources, sending operator messages and collecting data about process variables. With regard to allocating resources, several different pieces of equipment may be available for performing a particular function in a batch process. In a hardware allocation BMA, a particular piece of equipment may be selected in the manner described below. The graphical blocks can be combined in any sequence supported by the batch resources, i.e., the process cell, the DCS 30, etc. A graphical block for an operation causes the DCS 30 to perform a control action (such as opening a valve 42) or retrieve process data (such as a pressure or a temperature of a fluid). The graphical programming routine permits recipes to be configured as single threads of processing, branched logic, or parallel operations. When a batch is being run by the batch system 32, an operator may monitor the progress of the batch by viewing a copy of the RPD 120 for the batch created during recipe configuration.

A batch overview window (not shown) provides access to the batch operation functions and provides a summary of all the batches in the production schedule. Information about the batches is provided in a scroll-down table, wherein the rows represent batches, respectively, and the columns represent different types of information about the batches, respectively. The different types of information include: batch identification, lot identification, campaign identification, recipe identification, batch priority, batch state (i.e., running, aborted, pausing, etc.), mode of operation (i.e., automatic, manual, or semi-automatic), schedule status (i.e., not scheduled, scheduled, active, input pending), and start and end times. Functions that can be accessed through the batch overview window include: scheduling a new batch, invoking a batch schedule window 124 to schedule a new batch, displaying an RPD 120 for a batch or sub-procedure, and responding to pending operator messages for a batch. The batch overview window can be accessed from a button 122 on the application bar 92.

Figure 9:
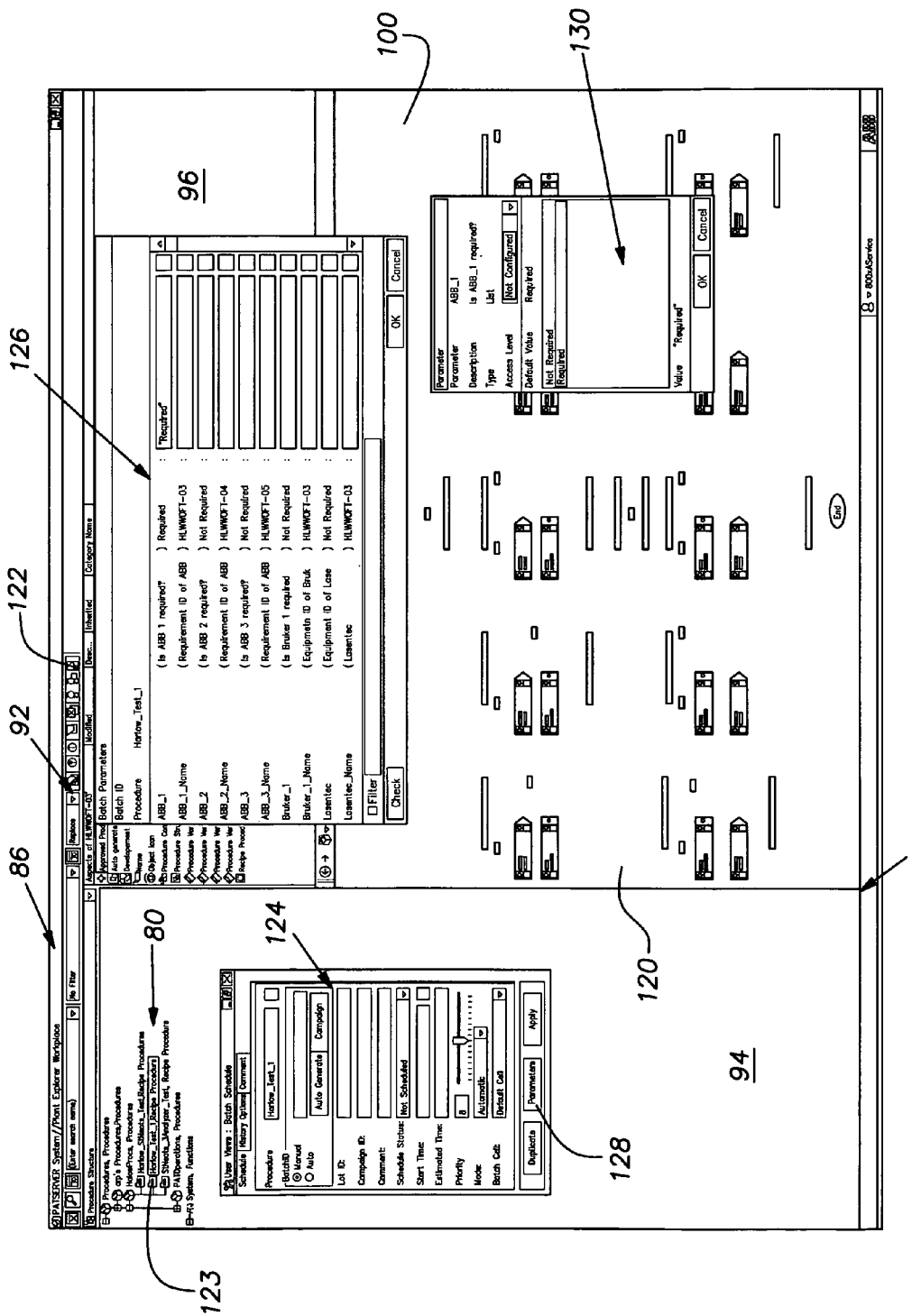
FIG. 9 is a screen shot of a second screen in the workplace in the graphical user interface.
Figure 10:
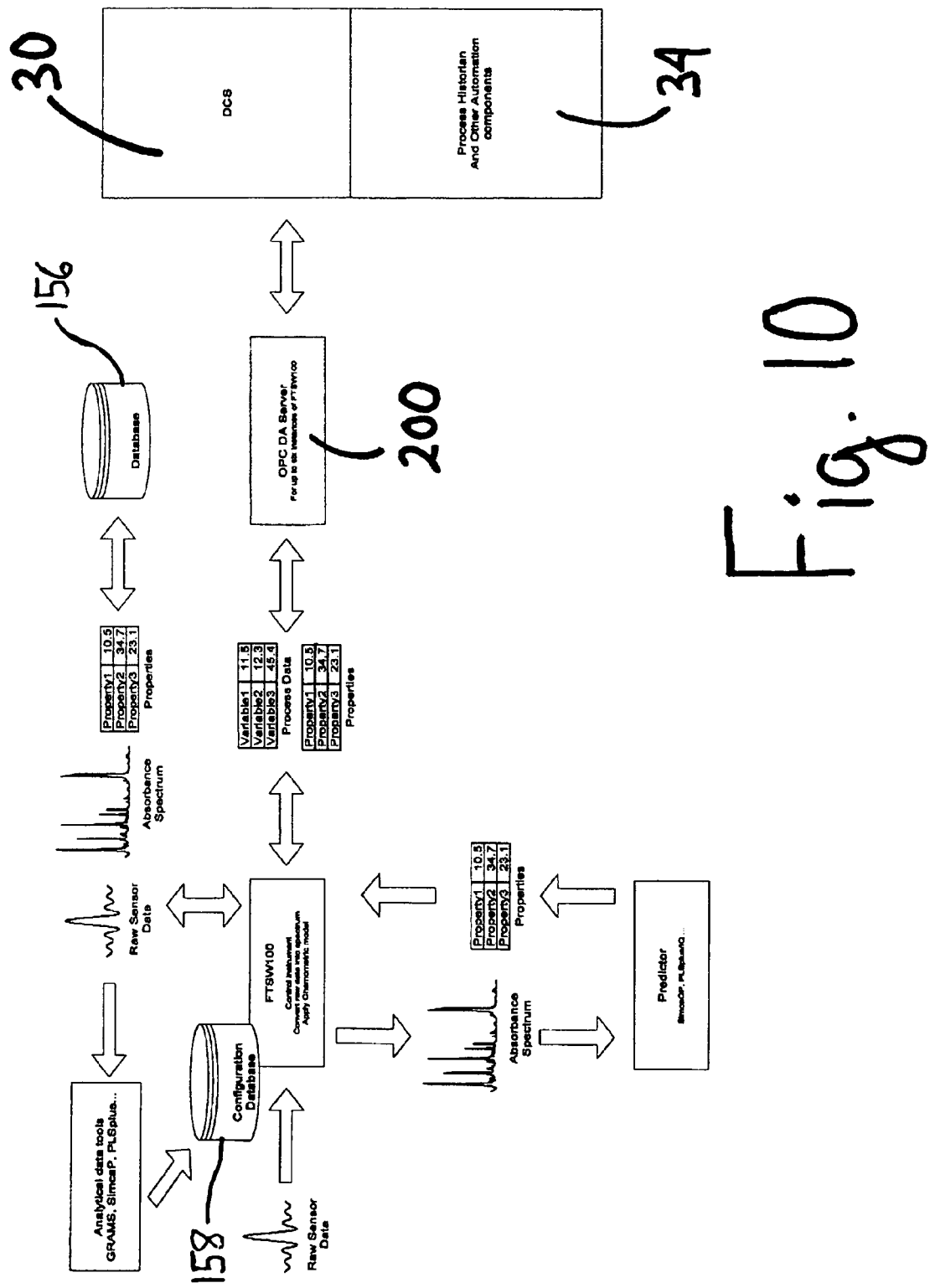
FIG. 10 is a schematic view of the flow of spectra data and sensor data through an analyzer controller.

Referring now to FIG. 9, there is shown a screen shot of the plant explorer workplace 86 showing a recipe called Harlow-_Test_1. In the object area 94, the object tree 80 contains an object 123 for the recipe. An RPD 120 for the recipe is shown in the preview area 100. The batch schedule window 124 has been invoked from the batch overview window. The batch schedule window 124 permits an operator to schedule a new batch of the recipe. The operator may set the parameters of the recipe for the new batch through a batch parameters window 126 that is accessed by clicking on a parameters button 128 in the batch schedule window 124. A piece of equipment, such as the spectrometer 140 designated HLWWOFT-03, may be selected for use in the new batch by entering the value "Required" in the box for the piece of equipment in the parameters window 126. The value is entered using a pop-up menu 130 that is accessed by clicking on a button 132.

Information Management System

Figure 8:
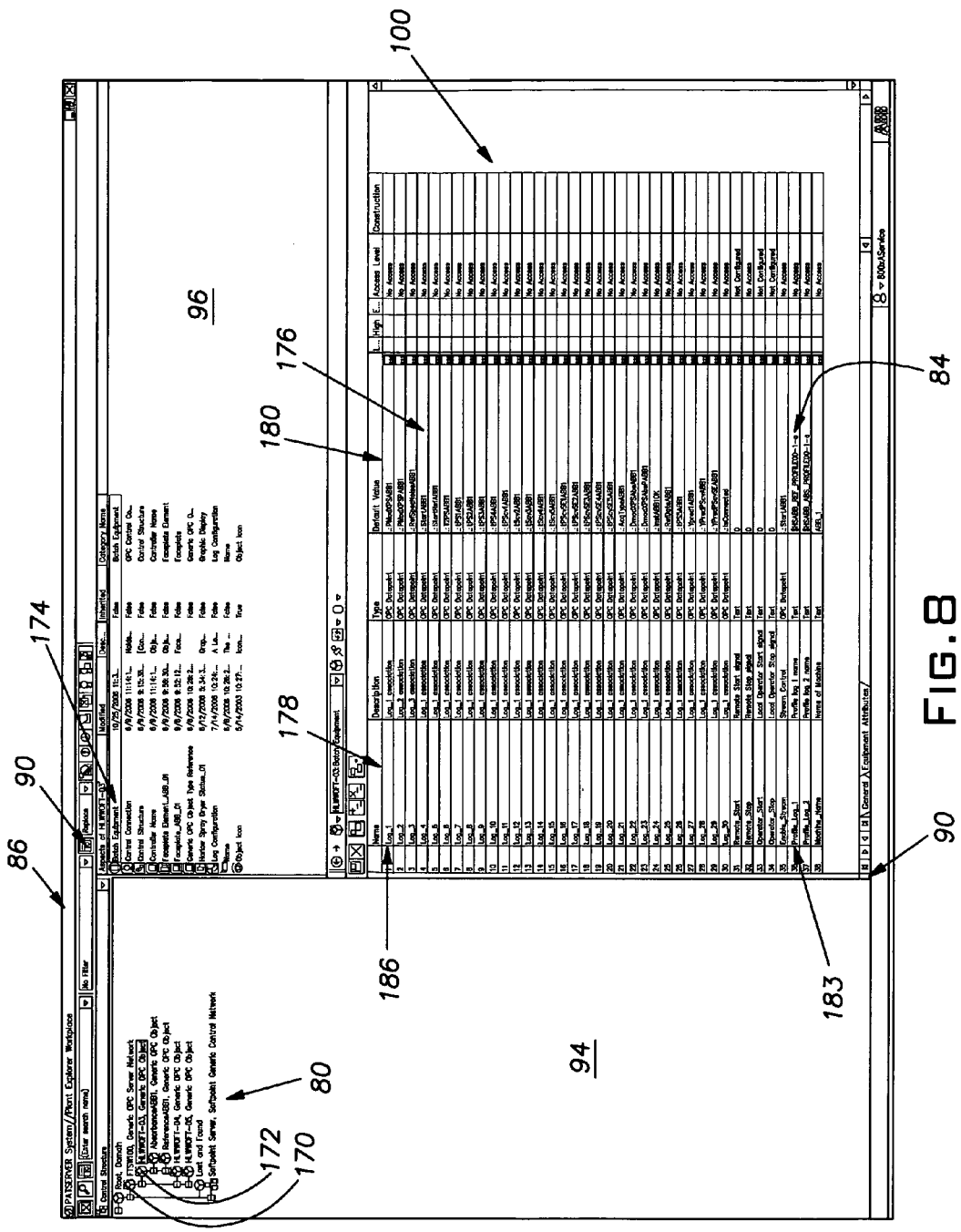
FIG. 8 is a screen shot of a first screen in a workplace in a graphical user interface of the automation software system.

The information management system 34 is a software system running on the server computer 52. Information within the automation software system 39 is stored in a database of the information management system 34 using logs. Spectral data, such as absorption spectrums, are stored as profile logs, while sensor data, such as temperatures, pressures, etc. are stored as numerical logs. The information management system 34 stores each profile log as a flat file, i.e., a file that contains records, wherein each record is set forth in a single line. Logs may be defined in the plant explorer workplace 86. Referring now to FIG. 8, there is shown a screen shot of the plant explorer workplace 86, wherein the object tree 80 is a control structure showing a parent object 170 for an analyzer controller 142 called FTSW800. A child object 172 for a spectrometer 140 designated HLWWOFT-03 is selected to produce a list of all of the aspects of the child object 172 in the aspect list area 96. An aspect 174 of the object 170 called "Batch Equipment" is selected in the aspect list area 96 to produce a view 176 in which logs for the spectrometer 140 may be defined. The view 176 comprises a table having a column 178 for log name, a column 179 for showing the log type and a column 180 for log value. Logs for spectral data, composition data and sensor data from the spectrometer 140 may be defined in the view 176. For example, a profile log 182 (schematically shown in FIG. 4) for an absorption spectrum from the spectrometer 140 for a particular sample stream may defined in a row 183. For row 183, column 180 specifies a log value 184 ($HSABB_REF_PROFILE00-1-0) for the profile log 182. The log value 184 is the OPC data point designation for the profile log 182 in the information management system 34. As shown in column 179, the profile log 182 is a text file, which, as described above is a flat file that will include spectral data. For the numerical logs, such as for sensor data and composition data, the log values in the column 180 are the OPC data point designations for the data in the information management system 34. The OPC data point designations for the numerical logs in the information management system 34 include the OPC data point designations for the data in the analyzer controller 142 associated with the spectrometer 140 designated HLWWOFT-03. Initially, the default log values for the OPC data point designations for the numerical logs in the information management system 34 are the OPC data point designations for the data in the analyzer controller 142. For example, a numerical log 185 (shown schematically in FIG. 4) and defined in row 186, has a default log value in column 180 of ":PMODXPSABB1", which is its OPC data point in the analyzer controller 142. In the information management system 34, the numerical log 185 will have an OPC data point name that includes ":PMODXPSABB1". More specifically, the OPC data point name will have ":PMODXPSABB1" plus a prefix. As shown in column 179, the numerical log 185 is an OPC data point, i.e., ":PMODXPSABB1".

Each time the information management system 34 receives a new absorption spectrum for the profile log 182 from the analyzer controller 142, the new absorption spectrum is entered into the profile log 182, along with a time stamp for the new absorption spectrum. Thus, the profile log 182 contains a plurality of absorption spectrum entries, each with a time stamp. Each profile log in the information management system 34 may be accessed through its OPC data point.

In addition to storing profile logs containing spectral data, the information management system 34 also stores numerical logs for a batch containing sensor data (e.g., temperature, pressure, etc.) associated with a sample and its spectral data. The information management system 34 also stores batch management data (e.g., batch start, batch stop, batch abort, batch runtime, equipment used, etc.) for a batch in PDL tables. The sensor data stored in the information management system 34 and associated with the spectral data may be obtained from the analyzer controllers 14 or more directly from the process control system 34.

Analyses of one or more samples from a batch may be performed in a laboratory after the batch has been completed. The laboratory analysis data may be entered into the automation software system 39 through the GUI 66 of the client work station 50. When the laboratory data is entered, it is associated with the spectral data for the batch by identifying the OPC data point for the profile log for the spectral data. The laboratory data is also stored in a log in the information management system 34.

For a particular batch, all of the equipment used in the batch (such as the spectrometer 140 designated HLWWOFT-03 and its associated analyzer controller 142) is known, as described above. Therefore, the logs and the OPC data points in the information management system 34 for all of the equipment used in a batch are also known. These OPC data points identify the logs stored in the information management system 34 that contain spectral data, sensor data and composition data for the batch. Since the batch start and stop times are also known, the spectral data in the profile logs for the batch can be identified using the time stamps in the profiled log. In this manner, spectral data, sensor data, composition data, laboratory data and batch management data that are stored in the database of the information management system 34 can all be associated with the batch and, thus, with each other.

Figure 11:
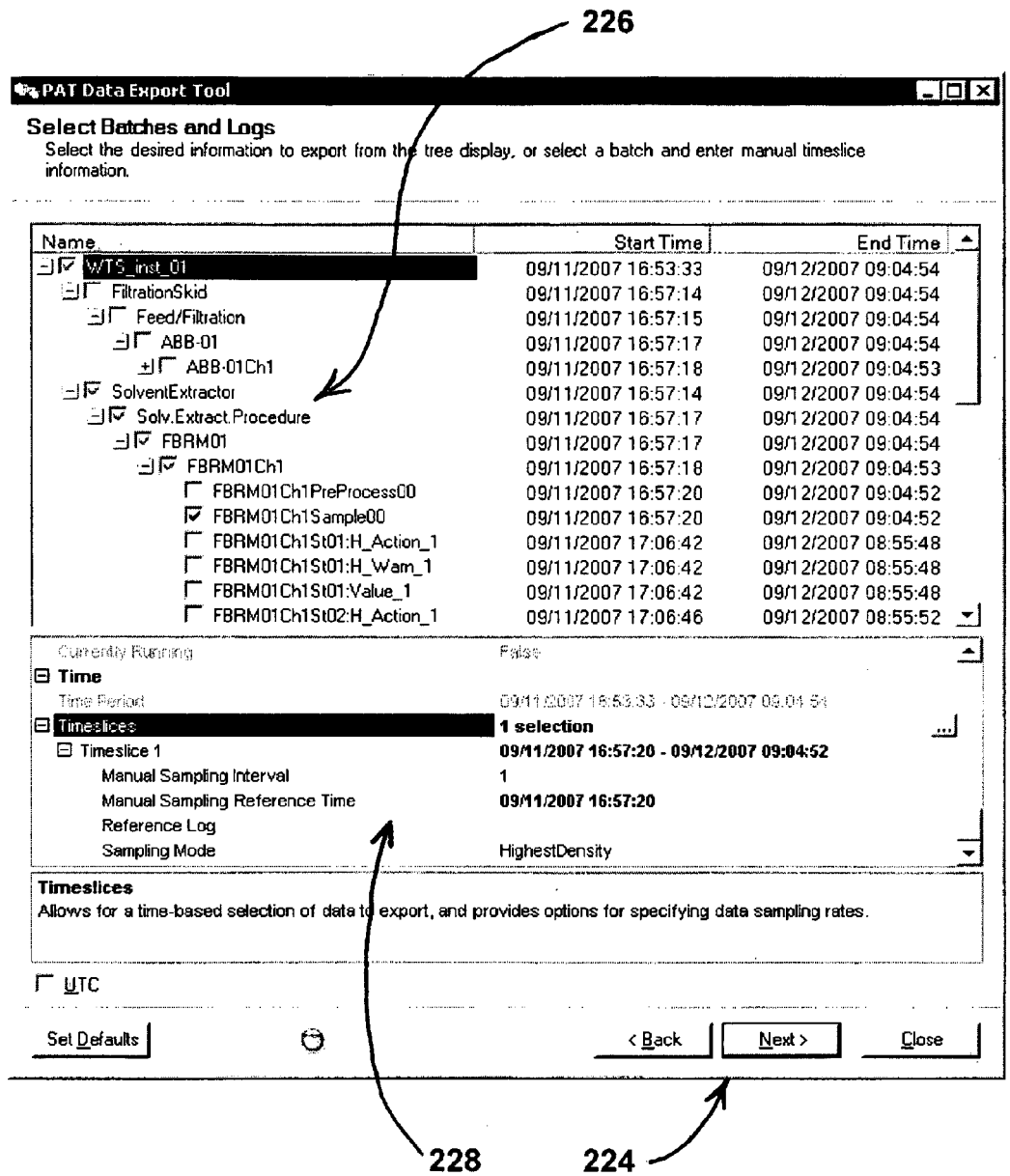
FIG. 11 is screen shot of a window in a data export tool of the automation software system.

Referring now to FIGS. 7 and 11, the data export tool 220 is a software application that is stored in, and runs on, the client work station 50. The data export tool 220 may be accessed through the GUI 66. The data export tool 220 is operable to gather all data (spectral, sensor, etc.) for a particular batch for a particular time period (time slice) from the database of the information management system 34 and make this data available to the data visualization tool 222. As shown in FIG. 11, the data export tool 220 includes a window 224 having a tree 226 listing a plurality of batches for which data is available. Selection boxes are disposed adjacent to the listed batches, respectively. A particular batch is selected by checking its associated selection box. As shown in FIG. 11, a batch FBRM01Ch1Sample00 has been selected. A time slice selection box 228 is located below the tree 226 and permits a user to manually select a time slice of the selected batch for which data is desired. Once a batch and time slice have been selected and the window 224 is closed, the data export tool 220 gathers all data (spectral, sensor, etc.) for the selected batch for the selected time slice from the database of the information management system 34 and makes this data available to the data visualization tool 222.

Figure 12:
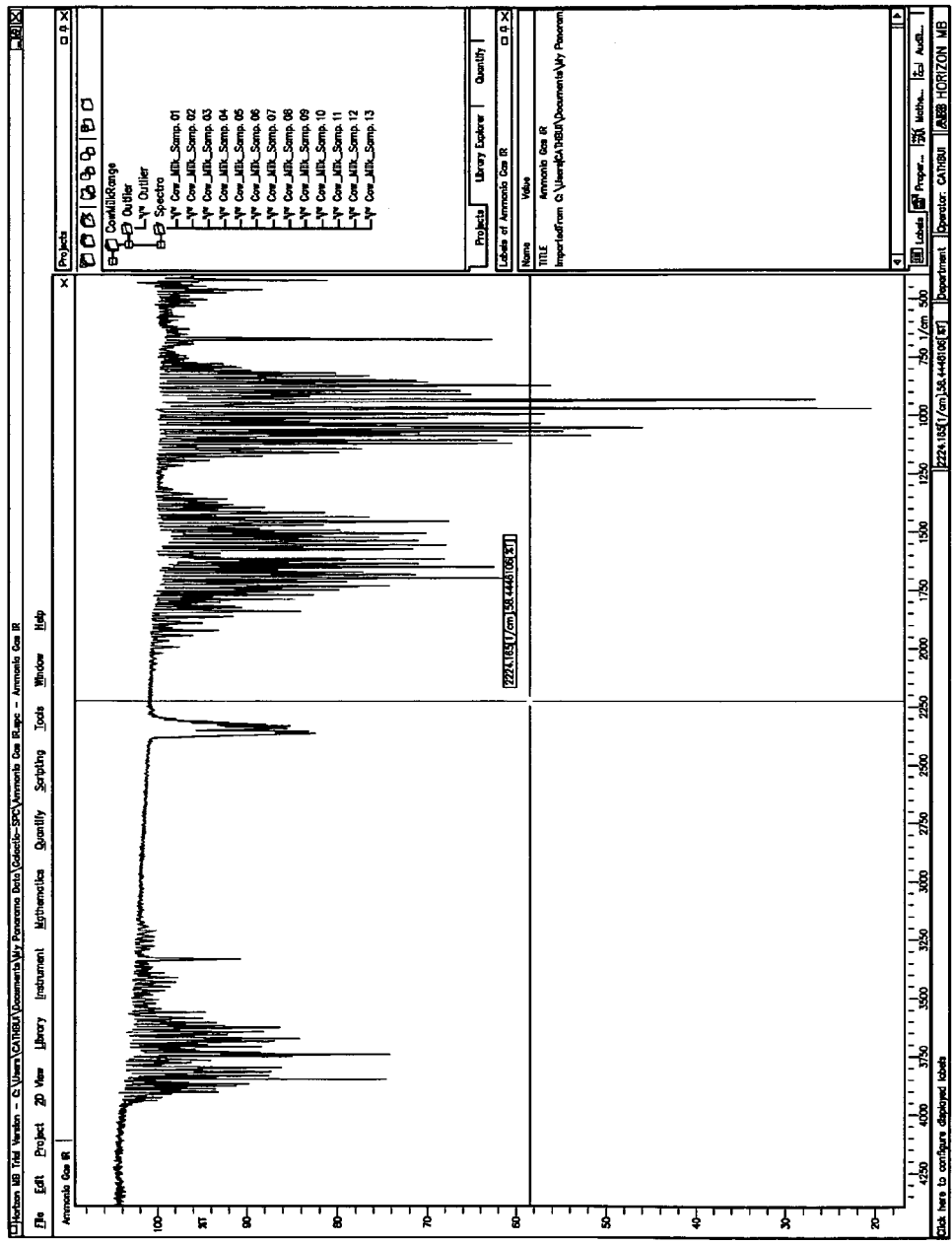
FIG. 12 is a screen shot of a first window in a data visualization tool of the automation software system, wherein the first window includes a two dimensional plot of spectral data.
Figure 13:
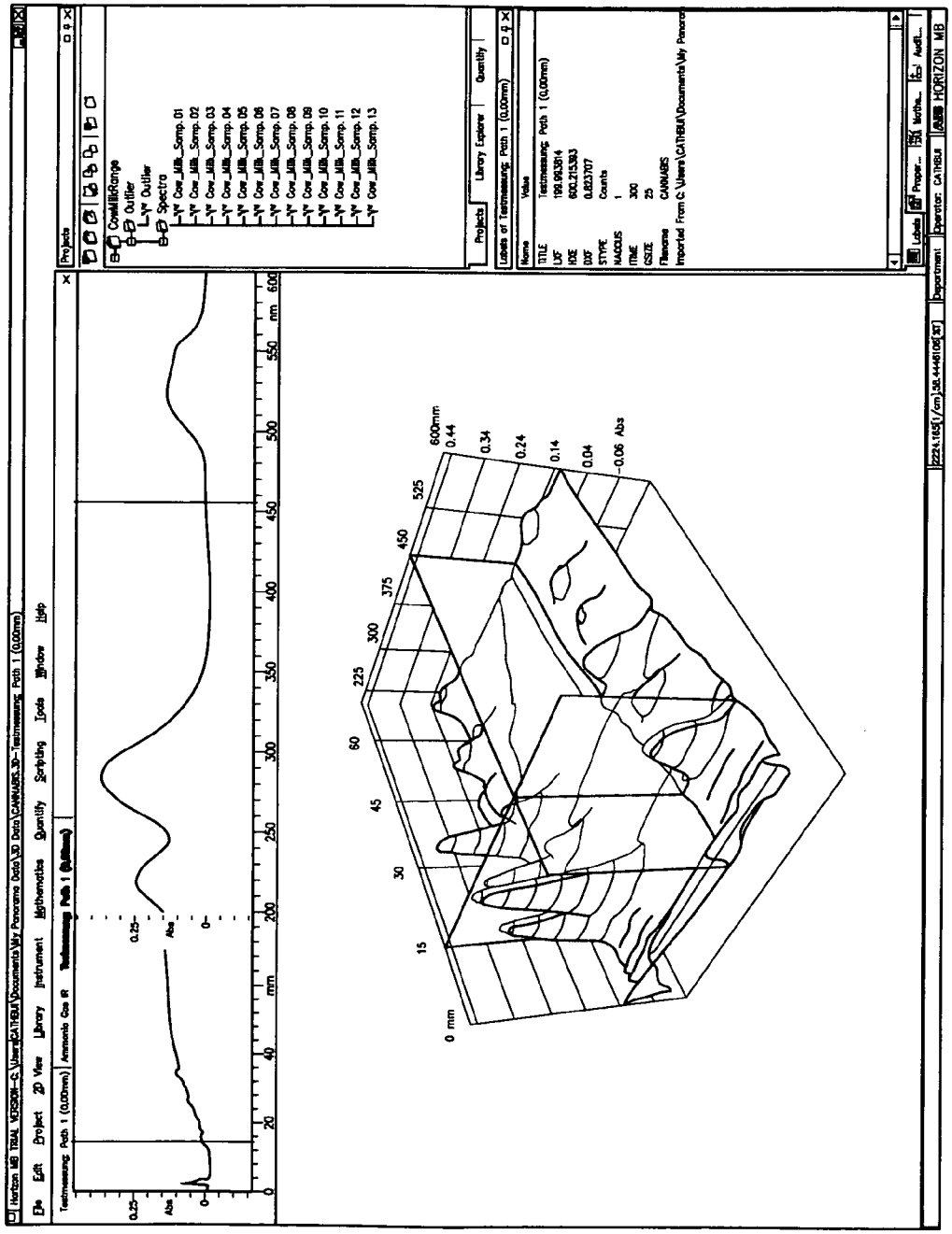
FIG. 13 is a screen shot of a second window in the data visualization tool of the automation software system, wherein the second window includes a three dimensional plot of spectral data.

Referring now to FIGS. 12 and 13, the data visualization tool 222 is a software application that is stored in, and runs on, the client work station 50. The data visualization tool 222 may be accessed through the GUI 66. The data visualization tool 222 is operable to display the spectral data for a selected batch for a selected time slice in a two dimensional plot (FIG. 12) or in a three dimensional plot (FIG. 13). The data visualization tool 222 also allows visualization of chemometric models as two dimensional or three dimensional scatter plots of the internal model variables (called principal components). Sensor data, batch management data and composition data associated with the spectral data for a selected batch for a selected time slice may be accessed in the data visualization tool 222 and displayed adjacent to the two or three dimensional plot of the spectral data.

In sum, the information management system 34 stores sensor data, batch data, spectral data, and additional computed composition properties associated with the spectrum as related data. It also stores the lab measurements, if any, associated with the spectral data. For certain processes which are continuous, virtual batches may be created based on time period.

The sensor data is published by the DCS 30 via OPC DA interface. Occasionally, the sensor data is scanned by the analytical data server 200 and published via OPC DA interface along with analyzer (spectrometer) measurements. This data is retrieved by the information management system 34 and stored as temporal data.

The batch events (mainly batch start/stop/abort and production line used) are generated by high-level applications such as the batch system 32, or occasionally by control systems. These events are published using the OPC AE interface. The events are retrieved and stored as structured data in the information management system 34.

The analyzer data server 200 provides the analyzer (spectrometer) measurements, along with instrument and stream identification and calculated material properties. Whenever a new spectrum measurement is available along with calculated material properties these are published. The information management system 34 retrieves this data and stores it.

The information management system 34 looks up the instrument and stream identification used by the running batches. The information management system 34 then associates the analyzer measurement, sensor data, and calculated material properties with the corresponding batch.

The lab measurements are entered using a graphical user interface. The spectrum identification is specified at the time of entering the lab data. The spectrum identification ties lab data with the corresponding spectrum data. The spectrum identification may be scanned using a bar code or radio frequency identification (RFID).

The sensor data, batch data, instrument/stream data and spectrum data are all stored in the information management system 34 as relational data. The graphical user interface makes it convenient to traverse data from a list of batches to a list of spectrum associated with a batch to spectrum measurement to material properties seamlessly.

The spectrum data and material properties data are published as OPC HDA interface.

It should be appreciated that in the foregoing description, the automation software system 39 and its components comprise software stored on computer readable medium (such as nonvolatile memory) in the server computer 52 or the client work station, as the case may be. This software includes program instructions that, when executed by a processor in the server computer 52 or the client work station, as the case may be, performs the functions described above with regard to the automation software system 39. Similarly, the controller software system 144 of analyzer controller 142 comprises software stored on computer readable medium (such as non-volatile memory) in the computer 146. This software includes program instructions, that, when executed by the processor 148 performs the functions described above with regard to the controller software system 144.

It should also be appreciated that the invention described above is not limited to use with an FTIR spectrometer, the invention may be used with any analyzer that produce array data to which a model is applied to determine various physical and chemical characteristics. Examples of other analyzers that may be used include:

FTNIR, IR, NIR, UV/Vis spectrometers
Raman spectrometers
Laser diffraction and image analysis particle size measuring systems
Liquid and gas chromatography
Acoustic spectroscopy
Terahertz spectroscopy
Mass spectroscopy
Nuclear Magnetic Resonance spectroscopy (NMR)
Laser Induced Fluorescence.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. A system for monitoring and controlling a batch process having field instruments and a sample system connected thereto, the field instruments being operable to measure process variables of the batch process and the sample system being operable to obtain a sample of material being produced by the batch process, the system comprising:

a control system for controlling the batch process, the control system being connectable to the field instruments to receive the measured process variables therefrom;

an analyzer connectable to the sample system to receive the material sample therefrom, the analyzer being operable to analyze the material sample and to generate array data representative of the composition of the material sample;

an analyzer controller connectable to the analyzer and to the control system and operable to collect the array data from the analyzer and the measured process variables from the control system;

at least one computer connectable to the analyzer controller and the control system;

a software data server stored on the at least one computer and executable to retrieve the array data and the measured process variables from the analyzer controller; and a software information management system stored on the at least one computer and including a database, the information management system being executable to receive the measured process variables and the array data from the data server and to store the measured process variables and the array data in the database in an associated manner; and a batch software system stored on the at least one computer and executable to store the identities of equipment used to monitor and control a batch run of the batch process, thereby associating the equipment with the batch run, and wherein the equipment used to monitor and control the batch run includes the analyzer; and wherein the array data and the measured process variables are each stored in the database so as to be associated with the analyzer, thereby causing the array data to be associated with the measured process variables.

2. The system of claim 1, wherein the array data comprises spectral data.

3. The system of claim 2, wherein the analyzer comprises a Fourier transform infrared (FTIR) spectrometer.

4. The system of claim 1, wherein the data server communicates with the analyzer controller using the TCP/IP protocol.

5. The system of claim 1, further comprising a software data export tool running on the at least one computer, the data export tool being operable to gather the array data and the measured process variables for the batch run for a particular time period from the database of the information management system.

6. The system of claim 5, wherein the at least one computer comprises a monitor for displaying information, and wherein the system further comprises a software data visualization tool running on the at least one computer, the data visualization tool being operable to display a plot of the array data gathered by the data export tool on the monitor.

7. The system of claim 6, wherein the plot is a two-dimensional plot.

8. The system of claim 6, wherein the plot is a three-dimensional plot.

9. The system of claim 6, wherein the data visualization tool is operable to display the measured process variables adjacent to the plot of the array data.

10. The system of claim 6, wherein the at least one computer comprises a first computer and a second computer having the monitor, the data export tool and the data visualization tool running on the second computer and the data server and the information management system running on the first computer.

11. The system of claim 1, wherein the array data is stored in the database in a flat file.

12. The system of claim 11, wherein the analyzer is operable to generate sets of array data, each set of array data representing the composition of the material sample at a different time period, and wherein the analyzer controller is operable to collect the sets of array data from the analyzer and the data server is operable to retrieve the sets of array data from the analyzer controller.

13. The system of claim 12, wherein the information management system is operable to receive each set of array data from the data server and to time stamp each received set of array data, and wherein each time stamped set of array data is stored in a single line in the flat file.

* * * * *

(12) EX PARTE REEXAMINATION CERTIFICATE (8610th)
United States Patent
Davidson et al.

(10) Number: US 7,756,657 C1
(45) Certificate Issued: Oct. 4, 2011

(54) SYSTEM FOR STORING AND PRESENTING SENSOR AND SPECTRUM DATA FOR BATCH PROCESSES

(75) Inventors: Mikael H. Davidson, Lakewood, OH (US); Hemant Kanodia, Solon, OH (US); Thomas Buijs, Quebec (CA); Claude LaFond, Quebec (CA)

(73) Assignee: ABB Inc., Norwalk, CT (US)

Reexamination Request:
No. 90/009,798, Sep. 16, 2010

Reexamination Certificate for:
Patent No.: 7,756,657
Issued: Jul. 13, 2010
Appl. No.: 11/939,696
Filed: Nov. 14, 2007

Related U.S. Application Data

(60) Provisional application No. 60/858,974, filed on Nov. 14, 2006.

(51) Int. Cl.
*G06F 19/00* (2006.01)
*G01N 37/00* (2006.01)
*G05B 21/02* (2006.01)

(52) U.S. Cl. .......................................... 702/83; 700/73
(58) Field of Classification Search .................. None
See application file for complete search history.

(56) References Cited

U.S. PATENT DOCUMENTS

| | | | |
|---|---|---|---|
| 4,976,542 A | 12/1990 | Smith | |
| 6,904,370 B1 | 6/2005 | Levinson et al. | |
| 2005/0038565 A1 | 2/2005 | Power et al. | |
| 2005/0143851 A1 | 6/2005 | Scalfani et al. | |
| 2005/0251278 A1 | 11/2005 | Popp | |

FOREIGN PATENT DOCUMENTS

EP 1 422 585 A2 5/2004

OTHER PUBLICATIONS

Characterizing Process Effects on Pharmaceutical Solid forms Using . . . , Roggo, et. al., Euro. Jour. of Pharmaceutics and Biopharmaceutics 61 (2005) 100–110 (Jul. 7, 2005).
Monitoring Complex Media Fermentations With Near–Infrared . . . , Ferreira, et. al., Biotechnology and Bioengineering, vol. 91, No. 4, (availible online Jun. 2, 2005).
FTIR and FT–PL Spectroscopic Analysis of TPV Materials and Devices, Webb, et. al., 4th Conf. on Thermophotovoltaic Generation of Electricity, Oct. 11–14, 1998, pp. 1–15.

*Primary Examiner* — Zoila Cabrera

(57) ABSTRACT

A system for monitoring and controlling a batch process. The system includes a control system that is operable to control the batch process and to receive measured process variables of the batch process. An analyzer analyzes a material sample from the batch process and generates array data representative of the composition of the material sample. An analyzer controller is operable to collect the array data from the analyzer and the measured process variables from the control system. A software data server running on a computer is operable to retrieve the array data and the measured process variables from the analyzer controller. A software information management system running on the computer is operable to receive the measured process variables and the array data from the data server and to store the measured process variables and the array data in a databased in an associated manner.

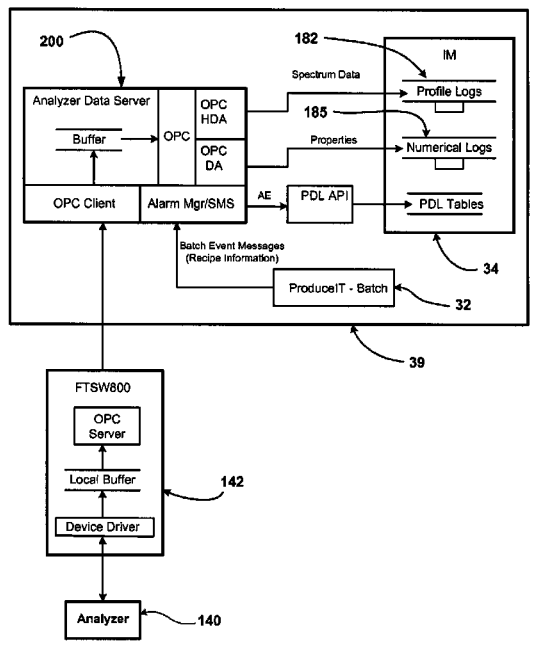

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentablity of claims 1-8 and 10-13 is confirmed.

Claim 9 was not reexamined.

* * * * *